United States Patent
Kim et al.

(10) Patent No.: US 9,383,319 B2
(45) Date of Patent: Jul. 5, 2016

(54) SUPER-RESOLVED OPTICAL IMAGING APPARATUS AND OPTICAL IMAGING METHOD USING THE SAME

(71) Applicant: Industry-Academic Cooperation Foundation, Yonsei University, Seoul (KR)

(72) Inventors: Dong Hyun Kim, Seoul (KR); Won-ju Lee, Seoul (KR); Youngjin Oh, Seoul (KR); Jong-ryul Choi, Seoul (KR); Taehwang Sohn, Gyeonggi-Do (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 168 days.

(21) Appl. No.: 14/142,030

(22) Filed: Dec. 27, 2013

(65) Prior Publication Data
US 2014/0209816 A1    Jul. 31, 2014

(30) Foreign Application Priority Data
Jan. 31, 2013  (KR) .......................... 10-2013-0010851

(51) Int. Cl.
*G01N 21/64*  (2006.01)

(52) U.S. Cl.
CPC .................................. *G01N 21/6456* (2013.01)

(58) Field of Classification Search
CPC .................................................. G01N 21/6456
See application file for complete search history.

(56) References Cited

U.S. PATENT DOCUMENTS

| | | | | |
|---|---|---|---|---|
| 4,758,727 A | * | 7/1988 | Tomei ................ | G01N 15/1468 250/458.1 |
| 5,365,076 A | * | 11/1994 | Itakura ................. | G01T 1/2012 250/582 |
| 2008/0230720 A1 | * | 9/2008 | Nielsen ............... | G01N 21/9027 250/492.1 |
| 2011/0240879 A1 | * | 10/2011 | Shiraishi et al. .......... | 250/432 R |
| 2013/0092823 A1 | * | 4/2013 | Amako et al. ................ | 250/216 |

* cited by examiner

*Primary Examiner* — Yara B Green
(74) *Attorney, Agent, or Firm* — Mintz Levin Cohn Ferris Glovsky and Popeo, P.C.; Kongsik Kim; Jonathon Western (57) ABSTRACT

A super-resolved optical imaging apparatus and a super-resolved optical imaging method using the apparatus are disclosed. The optical imaging apparatus can includes: a light source unit configured to supply an incident beam; a nano-pattern chip having a plurality of nanostructures; a light adjustment system configured to change an incidence property of the incident beam in at least one of a horizontal direction and a depth direction such that surface plasmon resonance occurs in a localized area of the plurality of nanostructures; and an image detection unit configured to extract fluorescence signals generated by the surface plasmon resonance from a specimen positioned in the localized area and convert the fluorescence signals into an image.

13 Claims, 8 Drawing Sheets

SUPER-RESOLVED OPTICAL IMAGING APPARATUS AND OPTICAL IMAGING METHOD USING THE SAME

CROSS-REFERENCE TO RELATED APPLICATIONS

This application claims the benefit of Korean Patent Application No. 10-2013-0010851, filed with the Korean Intellectual Property Office on Jan. 31, 2013, the disclosure of which is incorporated herein by reference in its entirety.

BACKGROUND

1. Technical Field

The present invention relates to super-resolved optical imaging, more particularly to an optical imaging apparatus and an optical imaging method using the apparatus that enable selective measurement along the horizontal and depth directions of a specimen.

2. Description of the Related Art

Biotechnology is fast rising as a next-generation industry, and accordingly, various bio-imaging techniques are being developed in the field of measurement systems.

The total internal reflection (TIR) imaging technique is a method of exciting a fluorescent substance by using evanescent waves that are formed when light undergoes total reflection. As the evanescent waves are formed within several hundreds of nanometers from a surface, it is possible to selectively excite only the fluorescent substance within a particular range. Because of this property, total internal reflection imaging may be utilized to study interactions at a particular interface, such as at a cell membrane, etc.

A conventional TIR microscope may be structured to excite a fluorescent substance dyed with a specimen, by using evanescent waves localized along the depth direction that are created when an incident beam undergoes total reflection at the interface between the specimen and a substrate, and to detect the fluorescence signals emitted from the excited fluorescent substance and convert them into an image. However, with the conventional TIR microscope, it is difficult or impossible to detect molecules or molecule trajectories, etc., in the horizontal direction which are smaller than the resolution limit that can be calculated by Abbe's equation of diffraction. Thus, there is a need for a TIR microscope that not only provides a high resolution in the depth direction but also provides a high resolution in the horizontal direction. Also, the conventional TIR microscope may not be able to provide selective excitation within the same surface.

SUMMARY

An aspect of the invention is to provide an optical imaging apparatus and an optical imaging method using the apparatus with which total reflection can be implemented that allows a high resolution not only in the depth direction from the surface of the sample specimen being measured, but also in the horizontal direction.

Thus, an aspect of the invention makes it possible to provide selective incident-beam excitation at a surface using a nano-pattern chip and a light adjustment system.

An aspect of the invention provides an optical imaging apparatus that allows imaging based on total internal reflection (TIR) with a high resolution not only in the depth direction but also in the horizontal direction.

An embodiment of the invention provides an optical imaging apparatus that includes: a light source unit configured to supply an incident beam; a nano-pattern chip having a plurality of nanostructures; a light adjustment system configured to change an incidence property of the incident beam in at least one of a horizontal direction and a depth direction such that surface plasmon resonance occurs in a localized area of the plurality of nanostructures; and an image detection unit configured to extract fluorescence signals generated by the surface plasmon resonance from a specimen positioned in the localized area and convert the fluorescence signals into an image.

Another aspect of the invention provides an optical imaging apparatus that allows TIR-based imaging with a high resolution not only in the depth direction but also in the horizontal direction.

An embodiment of the invention provides an optical imaging method that includes: changing an incidence property of an incident beam in at least one of a horizontal direction and a depth direction such that surface plasmon resonance occurs in a localized area of a plurality of nanostructures; and extracting fluorescence signals generated by the surface plasmon resonance from a specimen positioned in the localized area and converting the fluorescence signals into an image.

Changing the incidence property can include: changing a cross-sectional size and an incident path of the incident beam; and rotating the changed incident beam in a horizontal direction.

The optical imaging method can further include adjusting an incident angle of the incident beam, before or after the rotating in a horizontal direction.

With an optical imaging apparatus and an optical imaging method using the apparatus according to an embodiment of the invention, total reflection can be implemented that allows a high resolution not only in the depth direction from the surface of the sample specimen being measured, but also in the horizontal direction.

Also, it is possible to provide selective incident-beam excitation within a sample specimen using a nano-pattern chip and a light adjustment system.

Additional aspects and advantages of the present invention will be set forth in part in the description which follows, and in part will be obvious from the description, or may be learned by practice of the invention.

DETAILED DESCRIPTION

As the present invention allows for various changes and numerous embodiments, particular embodiments will be illustrated in the drawings and described in detail in the written description. However, this is not intended to limit the present invention to particular modes of practice, and it is to be appreciated that all changes, equivalents, and substitutes that do not depart from the spirit and technical scope of the present invention are encompassed in the present invention. In describing the invention, detailed explanations of relevant known technology will be omitted, if it is deemed that such explanations obscure the essence of the invention.

While such terms as "first" and "second," etc., may be used to describe various components, such components must not be limited to the above terms. The above terms are used only to distinguish one component from another.

The terms used in the present specification are merely used to describe particular embodiments, and are not intended to limit the present invention. An expression used in the singular encompasses the expression of the plural, unless it has a clearly different meaning in the context. In the present specification, it is to be understood that the terms such as "including" or "having," etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Certain embodiments of the invention will be described below in more detail with reference to the accompanying drawings.

Figure 1:
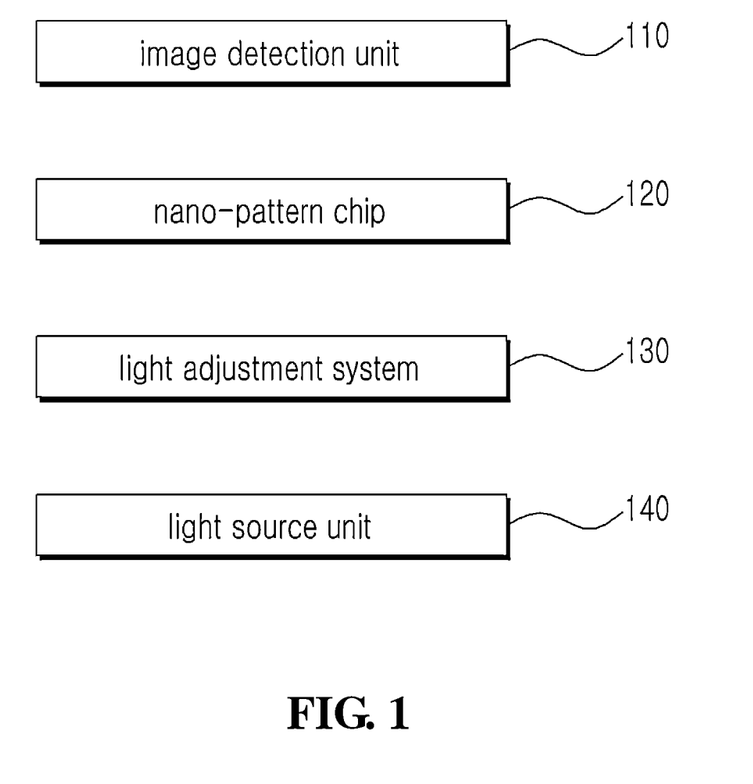
FIG. 1 is a block diagram of an optical imaging apparatus according to an embodiment of the invention.
Figure 2:
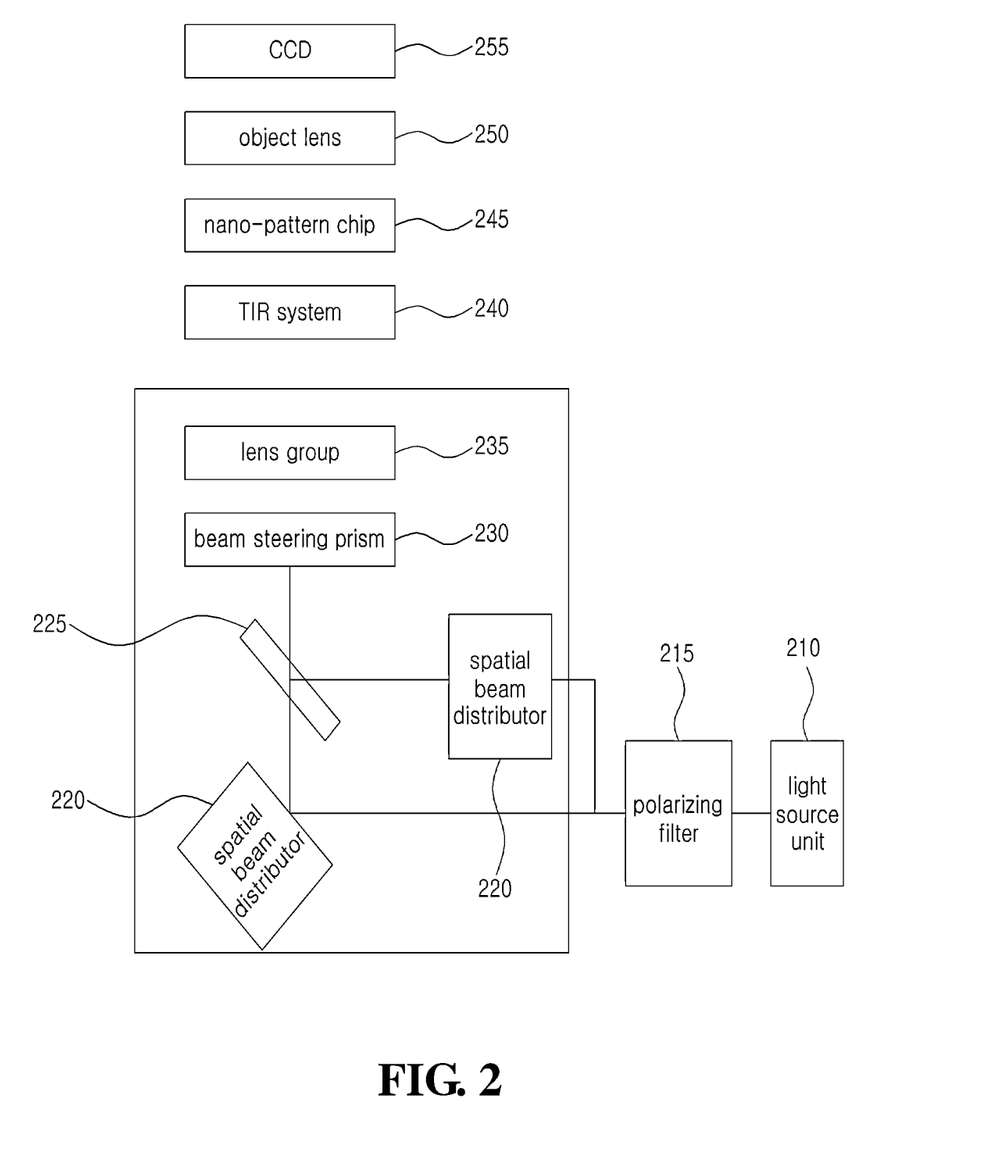
FIG. 2 illustrates the detailed composition of an optical imaging apparatus according to an embodiment of the invention.
Figure 3:
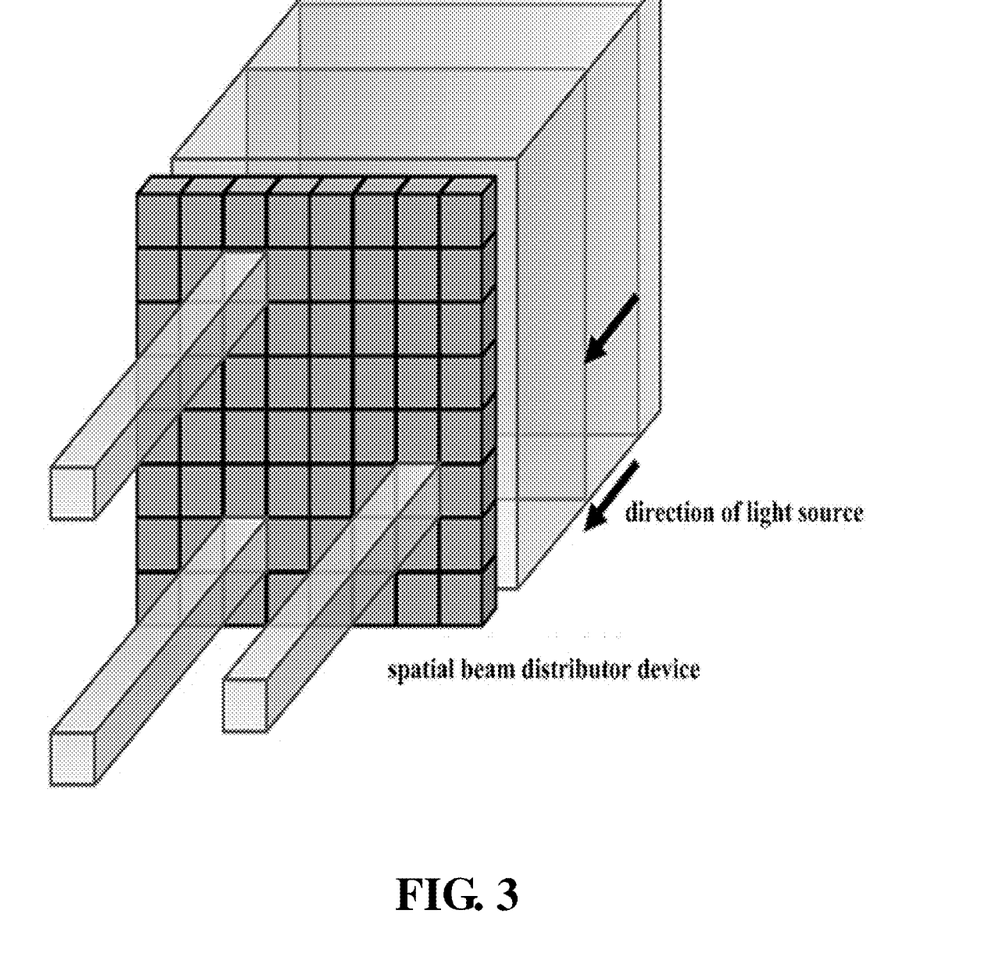
FIG. 3 illustrates the structure of a spatial beam distributor according to an embodiment of the invention.
Figure 4:
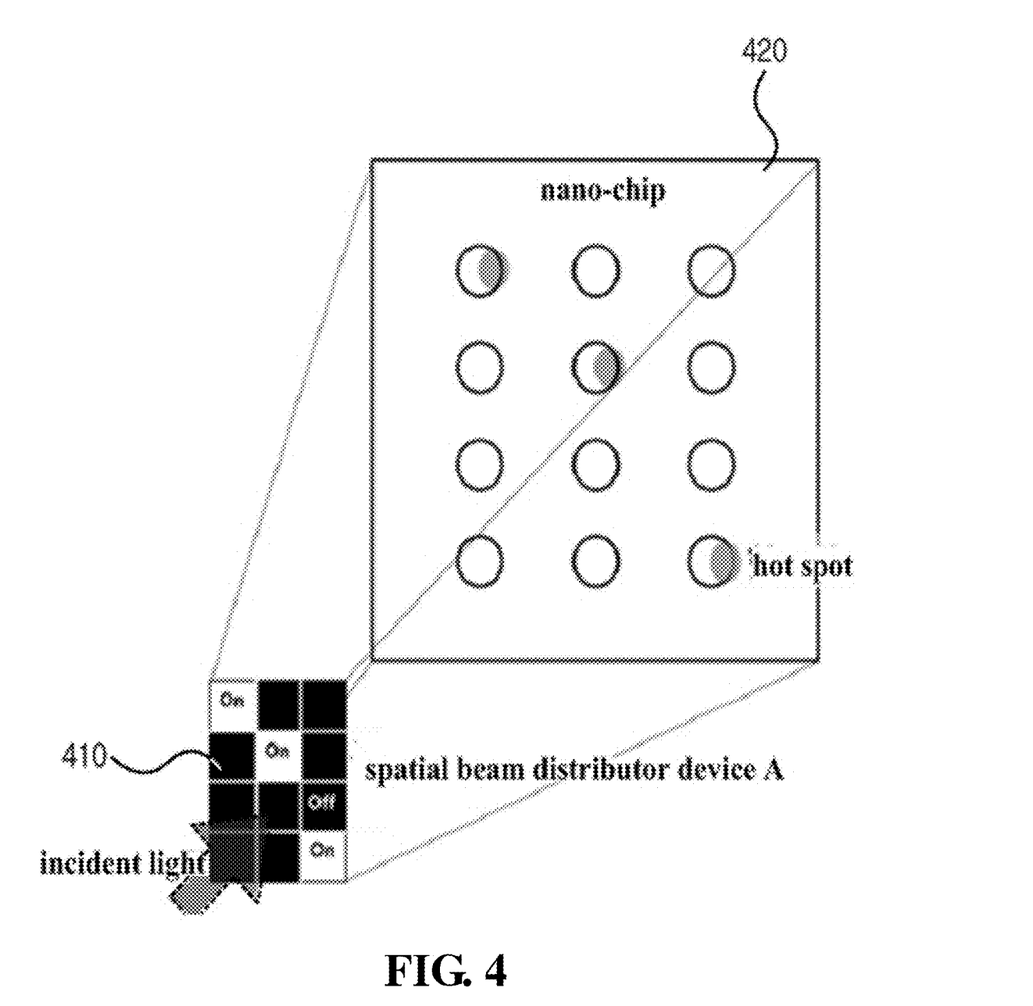
FIG. 4 and FIG. 5 illustrate the operation of a spatial beam distributor according to an embodiment of the invention.
Figure 5:
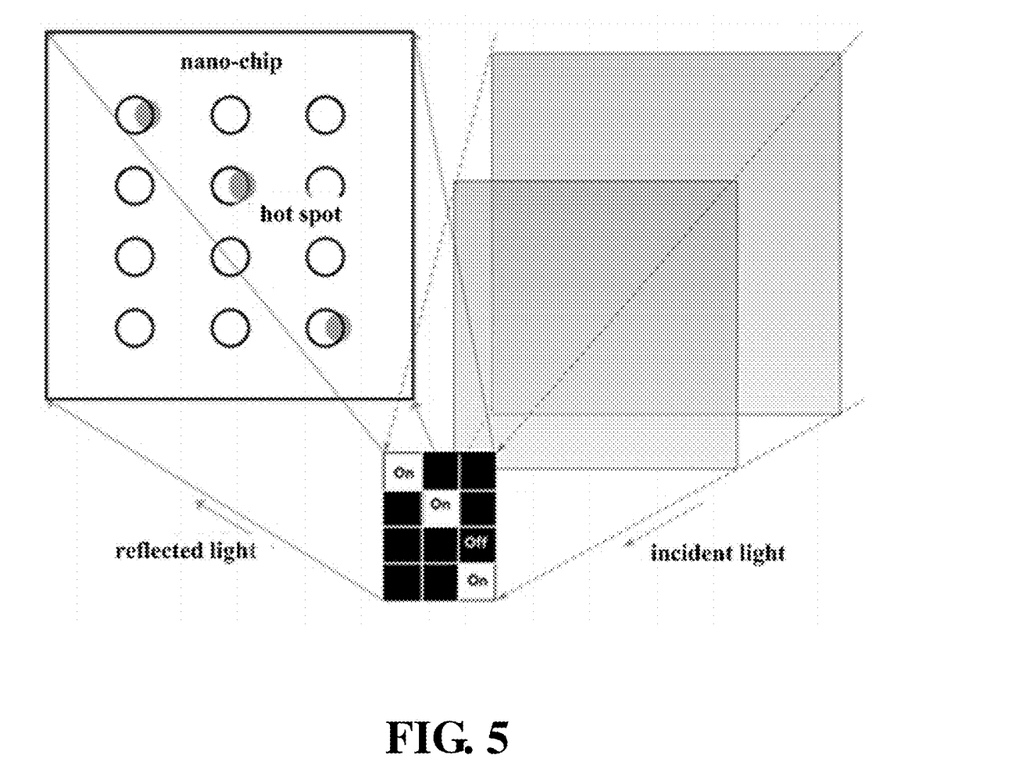
Figure 6:
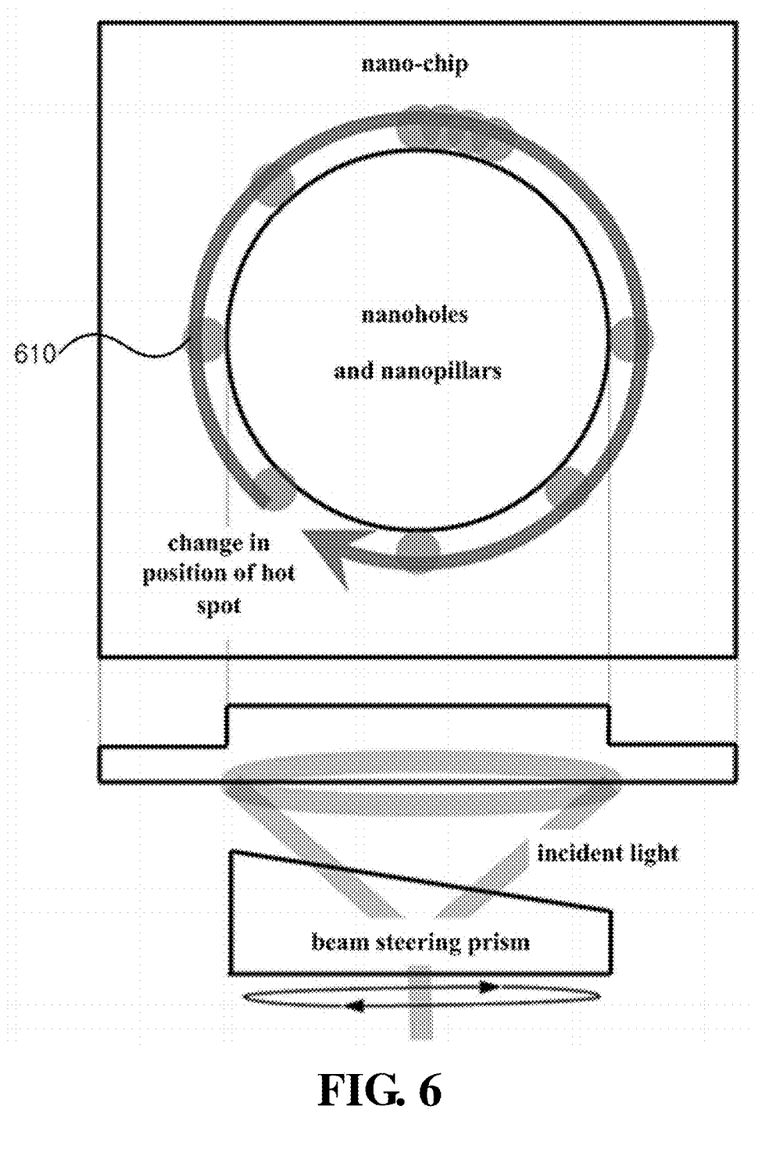
FIG. 6 illustrates the operation of a beam steering prism according to an embodiment of the invention.
Figure 7:
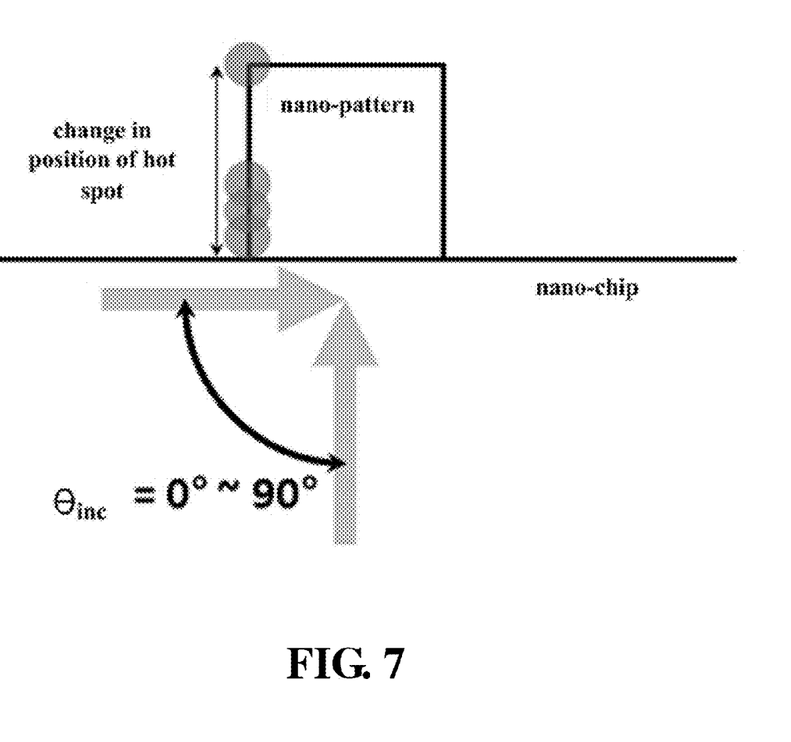
FIG. 7 illustrates the operation of an incident-angle adjustment system according to an embodiment of the invention.
Figure 8:
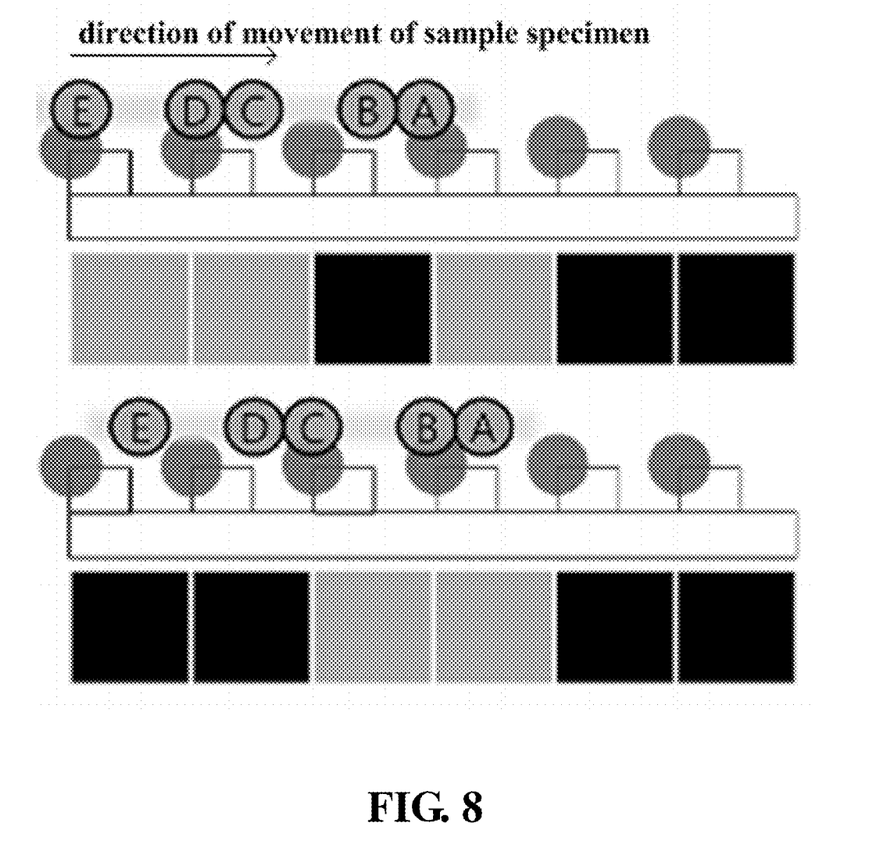
FIG. 8 illustrates a super-resolved image recovery method for a sample specimen displaying dynamic movement according to an embodiment of the invention.

FIG. 1 is a block diagram of an optical imaging apparatus according to an embodiment of the invention, FIG. 2 illustrates the detailed composition of an optical imaging apparatus according to an embodiment of the invention, and FIG. 3 illustrates the structure of a spatial beam distributor according to an embodiment of the invention. FIG. 4 and FIG. 5 illustrate the operation of a spatial beam distributor according to an embodiment of the invention, FIG. 6 illustrates the operation of a beam steering prism according to an embodiment of the invention, FIG. 7 illustrates the operation of an incident-angle adjustment system according to an embodiment of the invention, and FIG. 8 illustrates a super-resolved image recovery method for a sample specimen displaying dynamic movement according to an embodiment of the invention.

Referring to FIG. 1, an optical imaging apparatus according to an embodiment of the invention may include a nano-pattern chip 120, a light source unit 140, a light adjustment system 130, and an image detection unit 110.

The nano-pattern chip 120 may have a multiple number of nanostructures. Here, the multiple nanostructures can include irregularly arranged nanoislands, nanopillars, or nanoholes. Of course, the invention is not thus limited, and the multiple nanostructures can also include structures that are regularly arranged in a certain interval. The irregular nanostructures can be formed by forming a thin metal layer of silver (Ag) over a silver (Ag) thin film and heating to 150 to 200° C. Also, the nanostructures can also be formed by suitably heating a metal layer (e.g. an Ag layer) formed over an irregular nanohole-structure metal thin film.

In another example, a regularly arranged nanohole structure can be fabricated, for example, by electron beam lithography over a silver (Ag) thin film.

The nanostructures, such as nanoislands, nanopillars, or nanoholes, can be shaped as polygons, for example. Here, the polygons can be of various shapes, such as for example, triangles, rectangles, squares, rhombuses, circles, etc.

The multiple nanostructures can be made from at least one of silver (Ag), gold (Au), platinum (Pt), and aluminum (Al), or the multiple nanostructures can also be made from different metals.

The light source unit 140 may serve to provide a source of light that is to be incident on the nano-pattern chip 120. That is, an incident beam emitted by the light source unit 140 may be provided to the nano-pattern chip 120, and may generate surface plasmon resonance (SPR) in a localized area of the multiple nanostructures.

For easier understanding and explanation, a brief description of surface plasmon resonance is provided below.

The conditions under which the surface plasmon resonance phenomenon can be generated at the nano-pattern chip 120 can be obtained by RCWA (rigorous coupled wave analysis) or by FDTD (finite difference time domain) calculations. Known processes can be applied for forming the nano-pattern chip 120.

A plasmon refers to a quasiparticle resulting from free electrons within a metal oscillating collectively. In the nano-pattern chip 120, plasmons exist locally in the surface, hence the term surface plasmon. The phenomenon of the surface plasmons in the multiple nanostructures combining with an incident beam (photons) to create a strengthened electrical field is referred to as surface plasmon resonance (SPR), and the case of the surface plasmon resonance occurring in a localized area as in the present embodiment is referred to as localized surface plasmon resonance.

According to an embodiment of the invention, an incident beam may undergo total reflection at a lower part of the nano-pattern chip 120, and the evanescent waves generated by this total reflection may trigger surface plasmon resonance in a localized area.

Thus, an optical imaging apparatus according to an embodiment of the invention can be regarded as a TIR microscope in that total reflection is utilized for generating surface plasmon resonance.

A specimen dyed with a fluorescent material can be placed on a nano-pattern chip 120 according to an embodiment of the invention, and as the specimen (fluorescent substance) positioned in the local area where surface plasmon resonance occurs can be excited, fluorescent signals may be emitted.

The image detection unit 110 may serve to extract the fluorescent signals generated in the localized area in the nano-pattern chip 120 and convert the signals into an image.

The light adjustment system 130 may serve to alter the incidence properties of the incident beam emitted from the light source unit 140. Here, the incidence properties can include more than one of the cross-sectional size, incident path, incident direction, and incident angle of the incident beam. The light adjustment system 130 can direct the incident beam with altered incidence properties to the nano-pattern chip 120. That is, the light adjustment system 130 may provide the incident beam, of which the cross-sectional size and incident path is changed, and of which the incidence properties are changed in at least one of a horizontal direction and a vertical direction, to at least one of the multiple nanostructures of the nano-pattern chip 120. Thus, an incident beam can selectively reach certain nanostructures from among the multiple number of nanostructures, so that the number and positions of the localized areas can be selectively adjusted, thereby allowing surface plasmon resonance to occur in various localized areas through the changes in the horizontal and vertical directions.

FIG. 2 illustrates the detailed composition of an optical imaging apparatus according to an embodiment of the invention As illustrated in FIG. 2, the optical imaging apparatus can include a light source unit 210, a polarizing filter 215, a multiple number of spatial beam distributors 220, a mirror 225, a beam steering prism 230, a lens group 235, a TIR system 240, a nano-pattern chip 245, an object lens 250, and a camera 255.

The light source unit 210 may emit a laser beam (incident beam) of a particular wavelength, and the emitted incident beam may be polarized into a transverse magnetic (TM) mode by the polarizing filter 215. While it is not specifically illustrated in FIG. 2, the incident beam emitted by the light source unit 210 can also pass through a beam expander (not shown) before passing through the polarizing filter 215.

The incident beam that has passed through the polarizing filter 215 can have at least one of its cross-sectional size, incident direction, and incident angle adjusted by the light adjustment system 130.

The light adjustment system 130 may include at least one of spatial beam distributors 220, a mirror 225, a beam steering prism 230, and a lens group 235.

While FIG. 2 illustrates an example that includes a multiple number of spatial beam distributors 220, a light adjustment system 130 according to an embodiment of the invention can be operated with just one spatial beam distributor 220. That is, if there are multiple spatial beam distributors 220 included, as in the example shown in FIG. 2, it is possible to have just one of the multiple spatial beam distributors operational. Also, if there are multiple spatial beam distributors 220 included, as in the example shown in FIG. 2, one of the spatial beam distributors may pass the incident beam, while another may reflect the incident beam.

The spatial beam distributors 220 may serve to change the cross-sectional size and the incident path of the incident beam that has passed through the polarizing filter 215. A spatial beam distributor 220 may include a multiple number of beam distribution filters, as illustrated in FIG. 3. Here, a beam distribution filter can be implemented in the shape of a circle or an n-gon (where n is a natural number greater than or equal to 3). The spatial beam distributor 220 can include at least one beam distribution filter to be capable of changing the size of the cross section of an incident beam, and by passing through the beam distribution filter, an incident beam can be rendered a multiple number of incident paths each having a reduced cross section.

As illustrated in FIG. 4, for the multiple number of beam distribution filters 410 included in the spatial beam distributor 220, some of the beam distribution filters can be activated to pass or reflect incident light, in order that the incident beam may reach only some of the nanostructures of the nano-pattern chip 245.

FIG. 4 illustrates an example in which some of the beam distribution filters 410 of the spatial beam distributor 220 pass light, so that an incident beam can reach only some of the nanostructures.

FIG. 5 illustrates an example in which some of the beam distribution filters 410 of the spatial beam distributor 220 reflect light, so that an incident beam can reach only some of the nanostructures.

As illustrated in FIG. 4 and FIG. 5, the spatial beam distributor 220 can selectively activate some or all of the beam distribution filters 410, to change the incident path of an incident beam by passing or reflecting the incident beam, and can also reduce the cross-sectional size of the incident beam (see FIG. 4).

While FIG. 4 and FIG. 5 assume an example in which the beam distribution filters included in the spatial beam distributor 220 are shaped as n-gons, it is obvious that the beam distribution filters can also be implemented in a circular shape.

The incident beam, after having its cross-sectional size reduced and its incident path altered by the spatial beam distributor 220, can reach just some of the nanostructures of the nano-pattern chip 245, to generate surface plasmon resonance in a localized area. That is, the spatial beam distributor 220 can reduce the cross-sectional size of the incident beam and at the same time alter the incident path, to thereby adjust the number of hot spots (localized areas) created on the nano-pattern chip 245.

FIG. 4 and FIG. 5 illustrate examples in which the beam distribution filters of the spatial beam distributor 220 are controlled to change the incident path and the cross-sectional size of an incident beam. Although FIG. 4 and FIG. 5 illustrate examples in which the incident path is changed to three paths, respectively, it is obvious that the incident path can be altered in various other ways as well.

The incident beam of which the incident path and cross-sectional size are changed by the spatial beam distributor 220 may be reflected by a mirror 225 to arrive at the beam steering prism 230.

The beam steering prism 230 may undergo a horizontal rotation, so as to rotate the incident beam in a horizontal direction. Here, the horizontal rotation can be of an angle of 0 to 360 degrees. By rotating the beam steering prism 230, the positions of the localized areas of hot spots on nanostructures of the nano-pattern chip 245 selected by the spatial beam distributor 220 can be controlled along a horizontal direction.

FIG. 6 illustrates an example in which the positions of the hot spots on the nanostructures can be controlled along a horizontal direction by the horizontal rotation of the beam steering prism 230. That is, numeral 610 in FIG. 6 illustrates the change along a horizontal direction in the position of the hot spots on a nanostructure according to the rotation of the beam steering prism 230.

In this way, according to an embodiment of the invention, the number of hot spots on the nanostructures can be adjusted by using the spatial beam distributor 220 to change the cross-sectional size and the incident paths (number of hot spots) of an incident beam, so that an incident beam may selectively reach only the desired nanostructures, and the beam steering prism 230 can rotate the incident beams, of which the cross-sectional size and incident direction have been changed by the spatial beam distributor 220, to change the positions of the localized areas of hot spots on the nanostructures in a horizontal direction.

Thus, the incident beam rotated in a horizontal direction by the beam steering prism 230 may pass through the lens group 235 and be directed to the nano-pattern chip 245. The descriptions above focus on components for rotating an incident beam in a horizontal direction after its incident path and cross-sectional size are altered.

While it is not separately shown in FIG. 2, the incident angle of the incident beam in a vertical direction can be adjusted by a selective combination of the beam steering prism 230, lens group 235, and TIR system 240.

That is, by adjusting the steering angle of the beam steering prism 230 and the focal length of the lens group 235, it is possible to adjust the incident angle in the vertical direction. Here, an incident angle in the vertical direction can be any one of 0 to 89 degrees (see FIG. 7).

In the present disclosure, the beam steering prism 230, the lens group 235, and the TIR system 240 are collectively referred to as an incident-angle adjustment system for easier understanding and explanation. By thus adjusting the incident-angle adjustment system, the positions of hot spots can be adjusted in a vertical plane to obtain the desired height information of a sample specimen.

If the incident angle is adjusted to 0 degrees in the vertical direction, for example, the beam steering prism 230 of the incident-angle adjustment system can be detached, so that the incident beam may pass through the lens group 235 and through the TIR system to arrive at the nano-pattern chip.

In other examples for adjusting the incident angle in the vertical direction, the beam steering prism 230 can be attached, and the incident angle can be adjusted to a desired angle by controlling the beam steering prism 230, lens group 235, and TIR system 240.

FIG. 7 illustrates an example in which the incident angle is adjusted in a vertical direction according to an adjustment by the incident-angle adjustment system, so that the positions of hot spots on the nanostructures are altered in a vertical direction.

Thus, the light adjustment system 130 can adjust the cross-sectional size and the incident path of an incident beam that has passed through the polarizing filter 215, an can move the positions of the localized areas of hot spots on the nanostructures in a horizontal direction by changing the incident direction in the horizontal and vertical directions, thereby providing an optical image that has a high resolution in both the horizontal direction and the depth direction.

Referring again to FIG. 2, an incident beam that has passed through the beam steering prism 230 may then pass through a lens 235, and afterwards undergo total reflection by the TIR system 240, to arrive at the nano-pattern chip 245.

In this way, the light adjustment system 130 can change the incidence properties in one or both of the horizontal direction and the depth direction at the localized areas for certain nanostructures of the nano-pattern chip 245, so as to generate local surface plasmon resonance selectively.

An incident beam passed through the light adjustment system 130 may be totally reflected by the TIR system 240 and may arrive at the nano-pattern chip 245, to selectively generate local surface plasmon resonance in localized areas of certain nanostructures. Because of this, it is possible to recover a super-resolved image even for a sample specimen that displays a dynamic movement, as illustrated in FIG. 8.

The fluorescent signals of the specimen resulting from the local surface plasmon resonance generated selectively at localized areas of certain nanostructures of the nano-pattern chip 245 can be converted into an image through the object lens 250 and the camera (CCD) 255.

A super-resolved fluorescence imaging method that provides high resolution along the horizontal and depth directions according to an embodiment of the invention can be implemented in the form of program instructions that may be performed using various computer means and can be recorded in a computer-readable medium. Such a computer-readable medium can include program instructions, data files, data structures, etc., alone or in combination.

The program instructions recorded on the medium can be designed and configured specifically for the present invention or can be a type of medium known to and used by the skilled person in the field of computer software. Examples of a computer-readable medium may include magnetic media such as hard disks, floppy disks, magnetic tapes, etc., optical media such as CD-ROM's, DVD's, etc., magneto-optical media such as floptical disks, etc., and hardware devices such as ROM, RAM, flash memory, etc. Examples of the program of instructions may include not only machine language codes produced by a compiler but also high-level language codes that can be executed by a computer through the use of an interpreter, etc.

The hardware mentioned above can be made to operate as one or more software modules that perform the actions of the embodiments of the invention, and vice versa.

While the present invention has been described above using particular examples, including specific elements, by way of limited embodiments and drawings, it is to be appreciated that these are provided merely to aid the overall understanding of the present invention, the present invention is not to be limited to the embodiments above, and various modifications and alterations can be made from the disclosures above by a person having ordinary skill in the technical field to which the present invention pertains. Therefore, the spirit of the present invention must not be limited to the embodiments described herein, and the scope of the present invention must be regarded as encompassing not only the claims set forth below, but also their equivalents and variations.

What is claimed is:

1. An optical imaging apparatus comprising:
a light source unit configured to supply an incident beam;
a nano-pattern chip having a plurality of nanostructures;
a light adjustment system configured to change an incidence property of the incident beam in at least one of a horizontal direction and a depth direction such that surface plasmon resonance occurs in a localized area of the plurality of nanostructures; and
an image detection unit configured to extract fluorescence signals generated by the surface plasmon resonance from a specimen positioned in the localized area and convert the fluorescence signals into an image,
wherein the light adjustment system comprises a spatial beam distributor, the spatial beam distributor including a plurality of beam distributor filters and configured to change a cross-sectional size and an incident path of the incident beam by passing the incident beam through at least one of the beam distributor filters.

2. The optical imaging apparatus of claim 1, wherein the incidence property comprises more than one of a cross-sectional size, an incident path, an incident direction, and an incident angle of the incident beam.

3. The optical imaging apparatus of claim 1, wherein the spatial beam distributor is further configured to change the cross-sectional size and the incident path of the incident beam by reflecting the incident beam through at least one of the beam distributor filters.

4. The optical imaging apparatus of claim 3, wherein the beam distributor filter is shaped as an n-gon (where n is a natural number greater than or equal to 3) or a circle.

5. The optical imaging apparatus of claim 3, wherein the light adjustment system further comprises:
a beam steering prism configured to apply a horizontal rotation to rotate in a horizontal direction the incident beam having the cross-sectional size and the incident path thereof changed by the spatial beam distributor.

6. The optical imaging apparatus of claim 5, wherein the horizontal rotation is rotation by any one of 0 to 360 degrees.

7. The optical imaging apparatus of claim 3, further comprising:
an incident-angle adjustment system configured to change the incident angle of the incident beam having the cross-sectional size and the incident path thereof changed by the spatial beam distributor.

8. The optical imaging apparatus of claim 7, wherein the incident-angle adjustment system includes more than one of:
a beam steering prism configured to apply a horizontal rotation to rotate in a horizontal direction the incident beam having the cross-sectional size and the incident path thereof changed by the spatial beam distributor;

a lens group configured to refract the incident beam passed through the beam steering prism; and a TIR system configured to apply reflection by vertically rotating an incident angle of the incident beam refracted by the lens group.

9. The optical imaging apparatus of claim 8, wherein the vertical rotation is a rotation by any one of 0 to 89 degrees.

10. The optical imaging apparatus of claim 9, wherein the beam steering prism is detachably mounted.

11. The optical imaging apparatus of claim 10, wherein the beam steering prism is detached if the incident angle is adjusted to 0 degrees.

12. An optical imaging method comprising:

changing an incidence property of an incident beam in at least one of a horizontal direction and a depth direction such that surface plasmon resonance occurs in a localized area of a plurality of nano structures; and extracting fluorescence signals generated by the surface plasmon resonance from a specimen positioned in the localized area and converting the fluorescence signals into an image, wherein the changing of the incidence property comprises:

changing a cross-sectional size and an incident path of the incident beam; and rotating the changed incident beam in a horizontal direction.

13. The optical imaging method of claim 12, further comprising, before or after the rotating:

adjusting an incident angle of the incident beam.

* * * * *